(12) United States Patent
Afentakis

(10) Patent No.: US 9,949,683 B2
(45) Date of Patent: Apr. 24, 2018

(54) DUAL-FUNCTION ACTIVE MATRIX SENSOR ARRAY

(71) Applicant: Sharp Laboratories of America (SLA), Inc., Camas, WA (US)

(72) Inventor: Themistokles Afentakis, Camas, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 184 days.

(21) Appl. No.: 14/977,910

(22) Filed: Dec. 22, 2015

(65) Prior Publication Data

US 2017/0172489 A1 Jun. 22, 2017

(51) Int. Cl.
| | |
|---|---|
| *A61B 5/00* | (2006.01) |
| *G01K 7/16* | (2006.01) |
| *G01N 27/04* | (2006.01) |

(Continued)

(52) U.S. Cl.
CPC ............ *A61B 5/447* (2013.01); *A61B 5/6892* (2013.01); *G01D 1/00* (2013.01); *G01K 7/16* (2013.01);

(Continued)

(58) Field of Classification Search
None
See application file for complete search history.

(56) References Cited

U.S. PATENT DOCUMENTS 7,260,371 B1 * 8/2007 Yones .................. H04W 52/42
340/10.1
9,625,341 B2 * 4/2017 Haick .................. G01L 19/0092
(Continued)

FOREIGN PATENT DOCUMENTS

| JP | 8-29265 | 2/1996 |
|---|---|---|
| JP | 2006-343141 | 12/2006 |

OTHER PUBLICATIONS

R. Thomas, Does pressure cause pressure ulcers? Journal of the American Medical Directors Association, 11(6), 395-405, 2010.

(Continued)

*Primary Examiner* — Paresh Patel
(74) *Attorney, Agent, or Firm* — ScienBiziP, P.C.; Steve Reiss

(57) ABSTRACT

A method is provided for making multiple environmental measurements using a single sensing element. Each sensing element (sensel) includes a thin-film transistor (TFT) and a passive element. Typically, a plurality of sensels is provided arranged into an array. In response to an electrical stimulus, an electrical measurement is supplied that is responsive to a change in TFT electrical characteristic correlated to a first environmental condition, as well as a change in a characteristic of the passive element correlated to a second environmental condition. When the sensels are formed in an array, a plurality of electrical measurements is supplied corresponding plurality of locations on a monitored surface. Some exemplary environmental conditions include temperature, pressure, moisture, chemicals, oxygen, solution pH, salinity, and shear. The method determines the first environmental condition independent of the second environmental condition, while determining the second environmental condition independent of the first environmental condition.

23 Claims, 9 Drawing Sheets

(51) Int. Cl.
 G01D 1/00 (2006.01)
 G01K 7/22 (2006.01)
(52) U.S. Cl.
 CPC ........... *G01K 7/226* (2013.01); *G01N 27/045* (2013.01); *G01N 27/048* (2013.01); *A61B 2560/0252* (2013.01); *A61B 2562/029* (2013.01); *A61B 2562/0247* (2013.01); *A61B 2562/0261* (2013.01)

(56) References Cited

U.S. PATENT DOCUMENTS

| | | | |
|---|---|---|---|
| 2001/0004236 A1* | 6/2001 | Letkomiller | B60C 23/0408 340/572.1 |
| 2011/0274140 A1 | 11/2011 | Takatori | |
| 2016/0135749 A1* | 5/2016 | Chan | A61B 5/01 600/301 |
| 2016/0178798 A1* | 6/2016 | Holland | E21B 43/26 703/2 |

OTHER PUBLICATIONS

P. Slachta, Assessing risk of pressure- and moisture-related problems in long-term care patients, Wound Care Advisor, 2(3), 8-11, May/Jun. 2013.
http://www.healthleadersmedia.com/page-4/TEC-291902/Technology-Tackles-the-Pressure-Ulcer, May 7, 2013.
http://www.xsensor.com/Foresite, Jan. 15, 2015.
http://www.bruinbiometrics.com/images/Brochures/SEMScannerDeviceBrochure-Distributors_RevB.pdf, 5 pages.
http://news.berkeley.edu/2015/03/17/smart-bandages-detect-bedsores/.
Takao Someya et al., "A large-area, flexible pressure sensor matrix with organic field-effect transistors . . . ", Proc. NAS of the USA, Jul. 6, 2004, vol. 101 No. 27, pp. 9966.
Takao Someya et al. "Conformable, flexible, large-area networks of pressure and thermal sensors with organic transistor active matrixes", Aug. 2005.

* cited by examiner

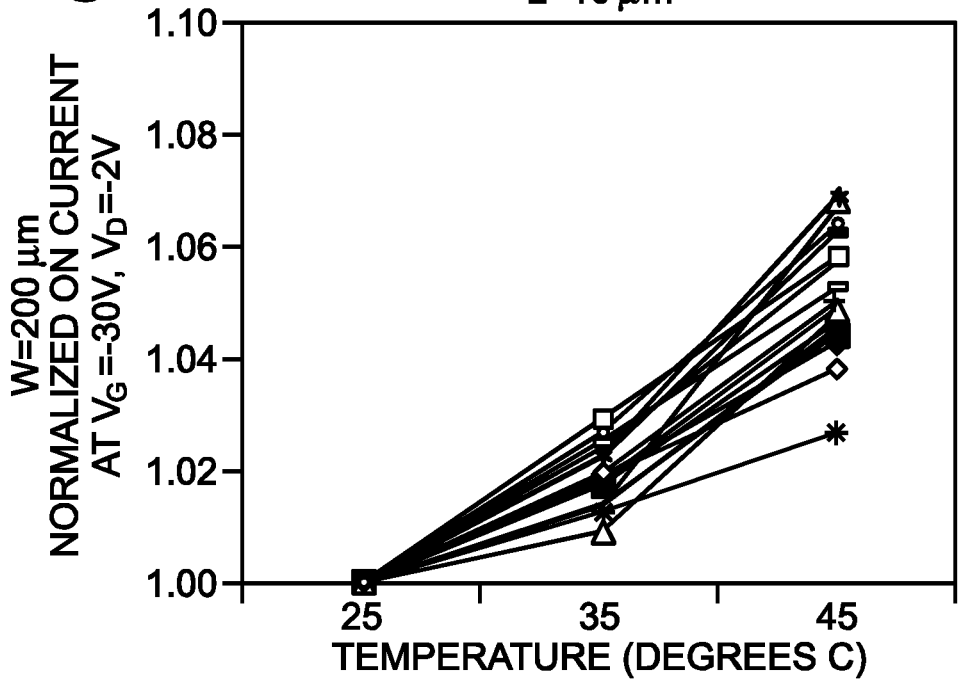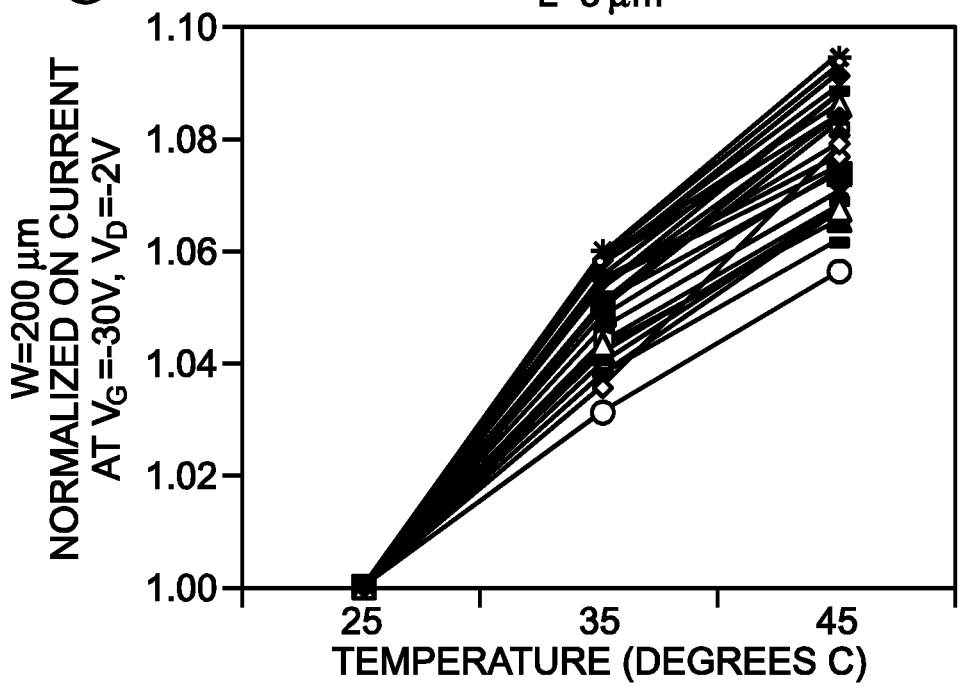

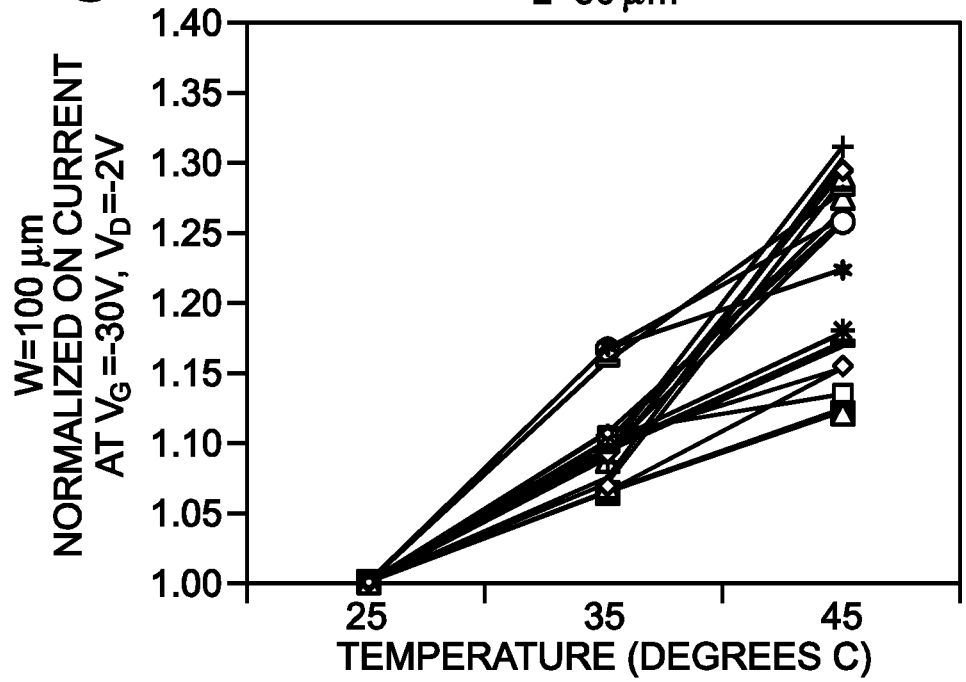
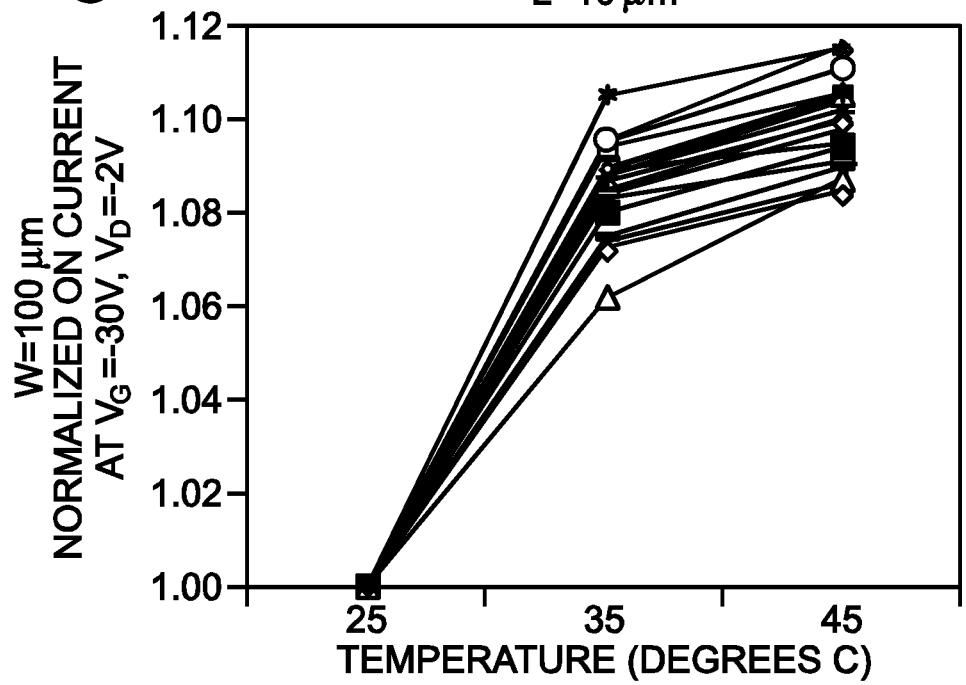

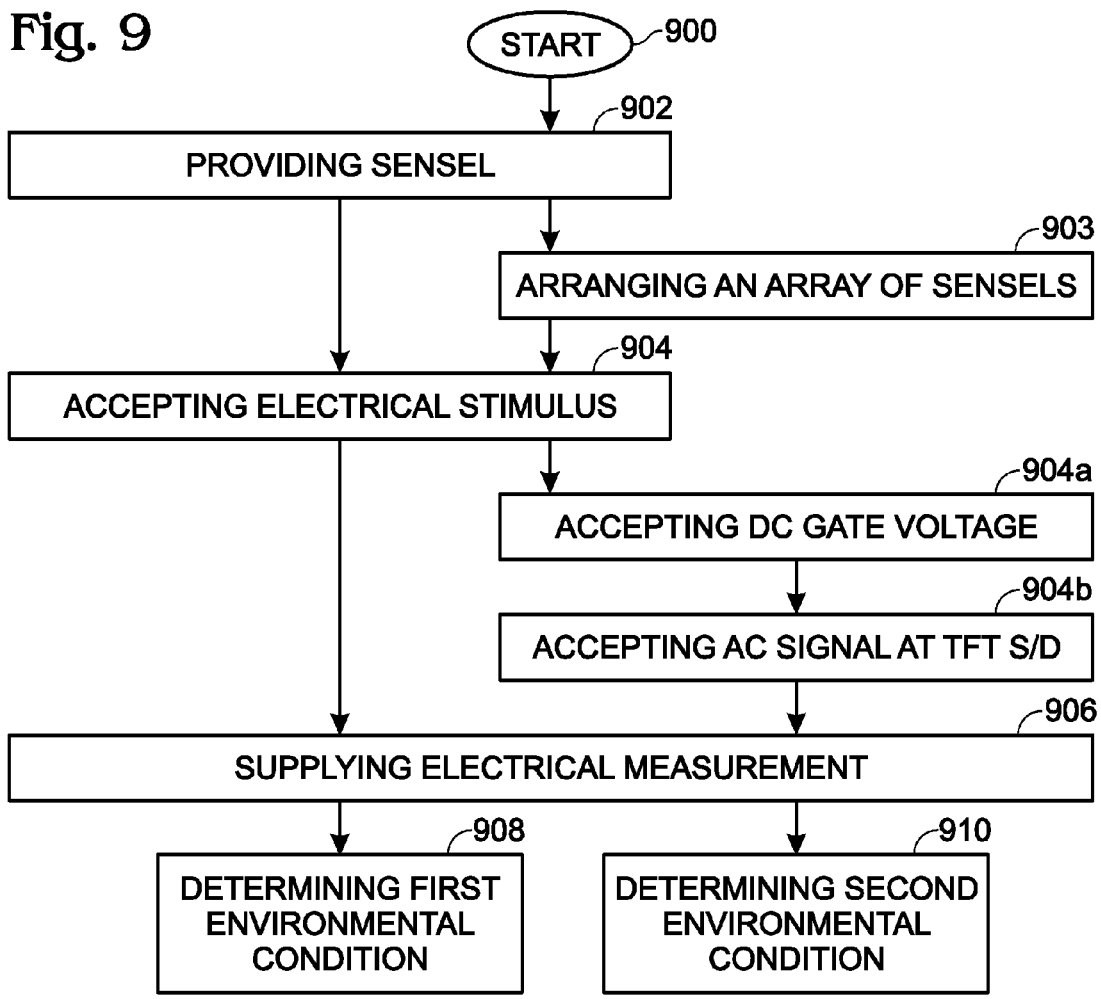

DUAL-FUNCTION ACTIVE MATRIX SENSOR ARRAY

BACKGROUND OF THE INVENTION

1. Field of the Invention

This invention generally relates to electronic array circuitry and, more particularly, to a sensor array able to monitor multiple environmental features with a single electrical measurement.

2. Description of the Related Art

Early detection of pressure ulcers is extremely important in order to avoid the onset of potentially life-threatening and costly problems. Pressure ulcers are caused by pressure against the skin (typically in areas of bone protrusions), which leads to localized ischemia and, ultimately, tissue necrosis. In 2007, there were 5.2 million cases of pressure ulcers worldwide; 2.4 million cases (60,000 resulting in death) in the US alone. According to a recent study (5,000 hospitals from 2003 to 2005), pressure ulcers have one of the highest occurrence rates, along with failure to rescue and postoperative respiratory failure. Pressure ulcer etiology is mostly associated with the following three factors: (a) pressure, (b) temperature, and (c) moisture.

Sustained pressure, leading to reduced blood flow in the skin or deep muscle tissue, is considered the prevalent factor. A commonly used pressure level of 35 millimeters of mercury (mmHg) is considered a danger threshold, which can be as high as 200 mmHg over a bony prominence[1]. Also, friction, leading to skin tissue damage, and shear are implicated. Regarding temperature, in healthy individuals, a local increase of skin temperature results in increased blood flow. In risk patients, blood flow is not adequate to reduce temperature. A skin temperature increase by 1.2° C. over 24/48 hours increases the risk of forming a pressure ulcer. Finally, increased moisture levels (e.g. perspiration, incontinence) makes the skin more susceptible to damage, as increased skin pH expedites cell deterioration[2].

This problem is currently addressed by electronic devices that measure specific metrics on the surface of the body. The majority of devices (proposed or currently in the market) involve detecting high pressure points. This is achieved by obtaining two-dimensional pressure maps of part of, or of the entire area of the body in contact with the surface upon which it rests (seat, bed mattress, etc.). Representative commercially available systems of this type are the Wellsense MAP® system[3] (a Class I exempt device, costing about $4,000 per year and comprising of "thousands" or sensor points), and the XSensor flexible capacitive pad system[4] (Costing $9,500-$12,000 per sheet, with 1,664 sensor points).

Other options include (a) measuring the impedance of the human skin as a function of frequency (spectroscopic impedance), in order to detect the onset of sub-epidermal tissue necrosis[5], and (b) the capacitive measurement of the sub-epidermal skin layers to detect changes in sub-epidermal moisture (SEM), a biophysical marker of damaged tissue[6].

It would be advantageous if a low-cost device existed that made the monitoring and detections of pressure-related environmental factors more practical.

[1] R. Thomas, Does pressure cause pressure ulcers?, Journal of the American Medical Directors Association, 11(6), 395-405, 2010

[2] P. Slachta, Assessing risk of pressure- and moisture-related problems in long-term care patients, Wound Care Advisor, 2(3), 8-11, May/June 2013

[3] http://www.healthleadersmedia.com/page-4/TEC-291902/Technology-Tackles-the-Pressure-Ulcer

[4] http://www.xsensor.com/Foresite

[5] http://www.bruinbiometrics.com/images/Brocures/SEM-ScannerDeviceBrochure-Distributors_RevB.pdf

[6] http://news.berkeley.edu/2015/03/17/smart-bandages-detect-bedsores/

SUMMARY OF THE INVENTION

Disclosed herein are a monitoring array and method that address the need for a product that aids in the early detection of pressure ulcers, or similar complications arising from sustained pressure points or other environmental factors on the human body. In particular, the array is a large surface area flexible electronic circuit, large enough to cover large areas of the body, or the entire body, which can provide real-time data via embedded sensors on a variety of metrics associated with the etiology of pressure ulcers. This data includes pressure/shear, temperature, moisture, pH, and others.

The flexible circuit electrically comprises the following components: (a) an active-matrix array, and (b) its scanning/read-out circuitry. The active-matrix array (a) comprises further of (i) one or more transistors in each sensing element (sensel) of the array, for activating that particular sensel, and (i) a capacitive or inductive sensor. All sensors of the array share the same transistor circuit architecture. However, the array may be enable one group of sensels employing a first type of capacitive sensors (e.g., for pressure monitoring), while another group of sensels employs a different type of capacitive sensors (e.g., for humidity monitoring).

In its simplest realization, the integrated sensor array element comprises of a thin-film transistor (TFT) and a passive element, such as a capacitor or an inductor. The purpose of this sensel is to simultaneously measure two physical quantities per sensel, such as temperature or pressure. This is contrasted with conventional methods where only one physical quantity is measured per sensing site.

The array achieves the simultaneous measurement of two physical quantities per sensel by utilizing the TFT device as both a sensor as well as an ON/OFF switching element. This is possible by engineering the TFT to have electrical characteristics when it is in the ON state that vary in response to a physical quantity X. At the same time, the passive element is engineered to have electrical characteristics that vary in response to a physical quantity Y. The sensitivity of the TFT to quantity Y is very low (ideally, zero), and likewise the sensitivity of the passive sensing element to quantity X is also very low (ideally, zero).

Accordingly, a method is provided for making multiple environmental measurements using a single sensing element. At least one sensel is provided including a TFT and a passive element. Typically, a plurality of sensels is provided arranged into an array. The sensel accepts a first electrical stimulus. In response to the first electrical stimulus, a first electrical measurement is supplied by the sensel that is responsive to a change in TFT electrical characteristic correlated to a first environmental condition, as well as a change in a characteristic of the passive element correlated to a second environmental condition. When the sensels are formed in an array, a plurality of electrical measurements are supplied responsive to first and second environmental conditions at a corresponding plurality of locations on the surface.

Some exemplary environmental conditions include temperature, pressure, moisture, chemicals, oxygen, solution pH, salinity, and shear. Accepting the first electrical stimulus may include the substeps of accepting a DC voltage at a gate electrode of the sensel TFT, while simultaneously accepting an AC signal at the drain electrode or source electrode of the sensel TFT. The AC signal is supplied at a first amplitude and a first phase. Then, supplying the first electrical measurement includes supplying the AC signal with a second amplitude, different than the first amplitude, and a second phase, different than the first phase. That is, the electrical measurement is derived from the change in amplitude and phase.

In response to supplying the first electrical measurement, the method determines the first environmental condition independent of the second environmental condition, while determining the second environmental condition independent of the first environmental condition. For example, the first electrical measurement may be responsive to TFT channel resistance or source-to-drain resistance ($R_{DS}$), which is in turn responsive to temperature as the first environmental condition. Other examples include: a TFT with a gate dielectric sensitive to a moisture first environmental condition, with the $R_{DS}$ responsive to changes in the moisture content of the gate dielectric; and, a TFT with a gate dielectric sensitive to a force or pressure first environmental condition, with the $R_{DS}$ responsive to changes in the force or pressure applied upon the gate dielectric region of the TFT. The sensel passive element may, for example, be a capacitor having a dielectric sensitive to a second environmental condition such as pressure, moisture, chemicals, solution pH, oxygen, salinity, or shear.

Additional details of the above-described method and a dual-function active sensor array are provided below.

BRIEF DESCRIPTION OF THE DRAWINGS

FIGS. 5A through 5F are graphs showing the variation of the normalized ON current of TFTs of various channel dimensions (width W and length L) as a function of temperature.

FIG. 9 is a flowchart illustrating a method for making multiple environmental measurements using a single sensing element.

DETAILED DESCRIPTION

Figure 1:
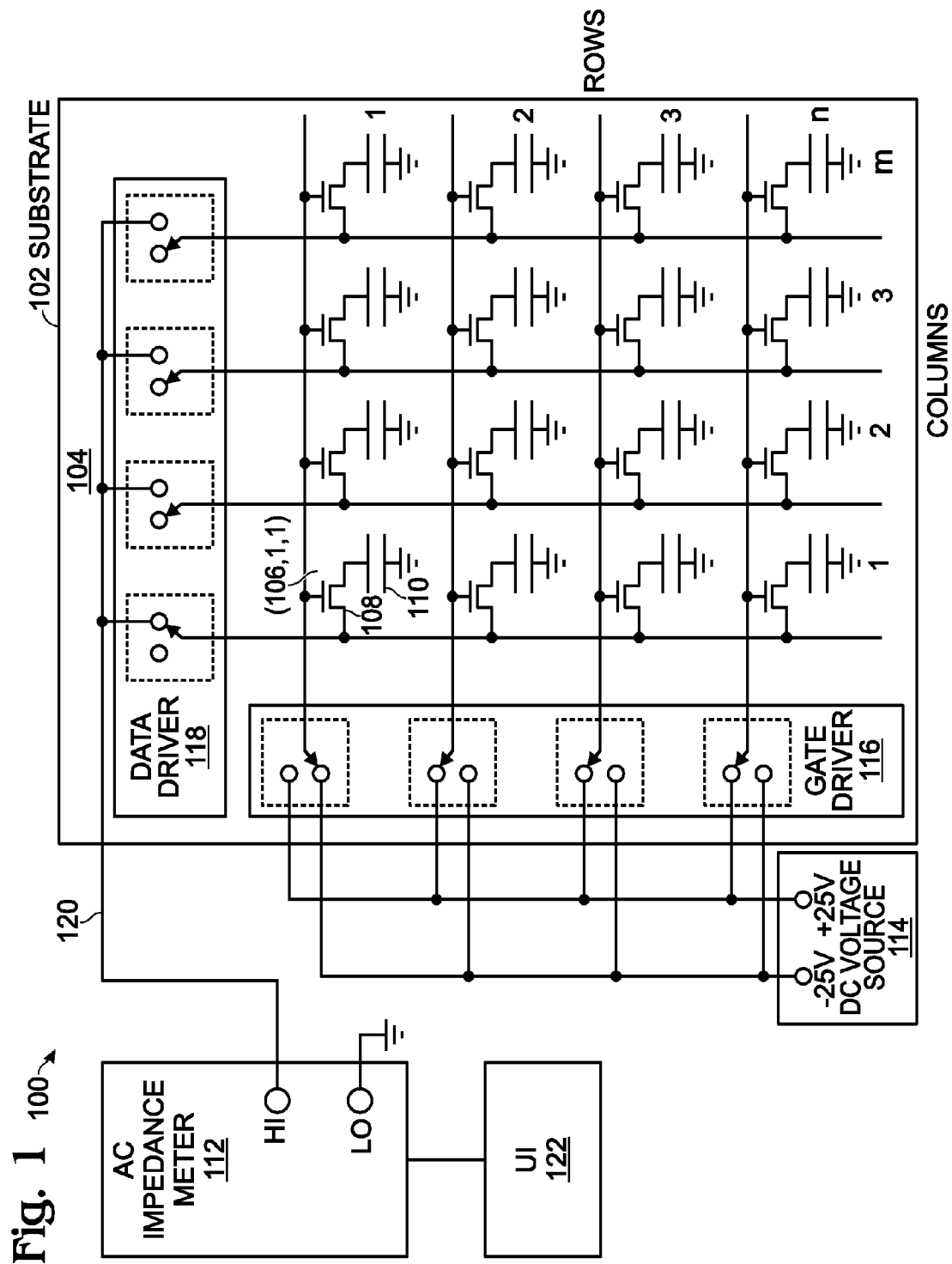
FIG. 1 is a schematic plan view of a dual-function active matrix sensor array.

FIG. 1 is a schematic plan view of a dual-function active matrix sensor array. The sensor array 100 comprising a substrate 102 with a top surface 104. A plurality of sensing elements (sensels) are formed in an array overlying the substrate top surface 104. Shown are sensels aligned in n rows and m columns, where n and m are positive integers. Individual sensor are identified with reference designator 106, row number, and column number, for example (106 n, m). In this example, n and m are both equal to 4, but these variables are not limited to any particular value. Using sensor (106 1, 1) as an example, each sensel comprises a thin-film transistor (TFT) 108 having a channel resistance or source-to-drain resistance ($R_{DS}$) responsive to a first environmental condition, and a passive element 110 having an AC impedance responsive to a second environmental condition, different than the first environment condition. Some examples of first and second environmental conditions include temperature, pressure, moisture, chemicals, oxygen, solution pH, salinity, and shear.

Here the passive element 110 is depicted as a capacitor. However, many other types of passive elements may also be used, such as a parallel-plate, co-planar interdigitated electrode, metal-oxide-semiconductor (MOS) capacitor, or an inductor. A measurement device 112 is selectively connectable to each sensel in the array to simultaneously determine first environmental condition measurements and second environmental condition measurements. In this example, the measurement device 112 is an alternating current (AC) impedance meter. As the measuring device of this example is an AC impedance meter, it also acts as a signal source. However, in other variations not shown, the signal source may be different than the measurement device.

The sensor array 100 also comprises a DC voltage source 114. A gate driver switching network (gate driver) 116 selectively connects a gate electrode of each sensel TFT to the DC voltage source 114. As shown, the gate driver 116 selectively connects sensels by the row. As shown, row 1 is connected to −25 volts to enable the transistors in row 1, while rows 2-n are connected to +25 volts to ensure that the transistors in these rows are off. The voltage values are exemplary and vary according to the type of TFT being used, the desired response time, and the desired voltages and currents of the signals to be measured. In one aspect, the DC voltages source 114 is a switched source, as it may not be necessary for the array to take constant measurements.

A data driver switching array (data driver) 118 selectively connects a drain (D) electrode or source (S) electrode of each sensel TFT to the measurement device 112, simultaneous with the gate driver switching network connecting the gate of the corresponding TFT to the DC voltage source 114. As shown, data driver 118 is enabling column 1 of the array 100. The combination of row 1 and column 1 being enabled means that the response of sensel (106 1, 1) is being measured.

In one aspect, the measurement device 112 supplies an AC signal on line 120 having a predetermined first amplitude and predetermined first phase, and makes a first environmental condition determination and a second environmental condition determination in response to detecting a change in AC signal. More explicitly, the measurement device 112 may make the first environmental condition determination and second environmental condition determination in response to detecting a change in the AC signal amplitude with respect to the AC signal first amplitude, and a change in AC signal phase with respect to the AC signal first phase. As shown, an AC impedance meter is able to make such a measurement. Alternatively, a network analyzer can be used.

The measurement device 112 is able to detect a first AC signal amplitude change and a first AC signal phase change, determine the first environmental conditions independent of second environmental condition measurements, and simultaneously determine the second environmental conditions independent of first environmental condition measurements.

In one variation the measurement device 112 supplies an AC signal at a plurality of frequencies, where each AC signal frequency has a predetermined amplitude and phase. Then, the measurement device 112 makes a first environmental condition determination and a second environmental condition determination in response to detecting a change in the plurality of AC signals. The use of multiple frequencies may be advantageous if the highest sensitivities of $R_{DS}$ and the passive element impedance are at different frequencies.

In one aspect, the measurement device 112 has a user interface (UI) 122 to supply a map of first and second environmental conditions, cross-referenced to sensel locations in the array. For example, the map can be depicted on a display. In one simple aspect, the UI 122 may simple be an (e.g., audio) alarm. In another aspect, the UI 122 may display the actual measurement or even a chart of measurement possibilities cross-referenced to first and second environmental conditions. Since the first environment condition measurement is independent of the second environmental condition measurement, the determination of environmental conditions from a change in amplitude and phase may require a matrix of amplitude/phase measurements cross referenced to first and second environmental conditions. For the sake of simplicity it is assumed that the measurement device is equipped with such a matrix or is otherwise able to make environmental determinations based upon mathematical formulas able to convert measured amplitude/phase changes. Otherwise, a calculating device (not shown) may be connected to the measurement device and UI to make such determinations.

In the general case, when only one or both the environmental conditions change, both amplitude and phase change. Since two environmental conditions are being detected, two measurements (amplitude and phase) are needed. This is the well-known two-equations with two-unknowns approach. If only one environmental condition is assumed to change, then it can be detected either by measuring amplitude or phase. If two environmental conditions change, then theoretically they cannot be measured by looking at one metric (amplitude alone, or phase alone). In the typical deployment scenario, it might be impossible to know a priori that one environmental condition remains constant. Therefore, in a typical case, both phase and amplitude must be measured.

Figure 3:
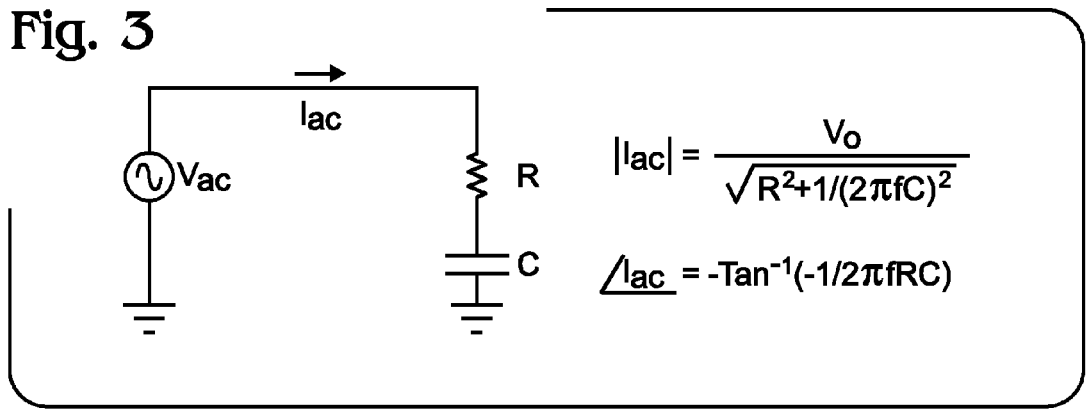
FIG. 3 is an equivalent circuit of the sensel depicted in FIG. 2.
Figure 5A:
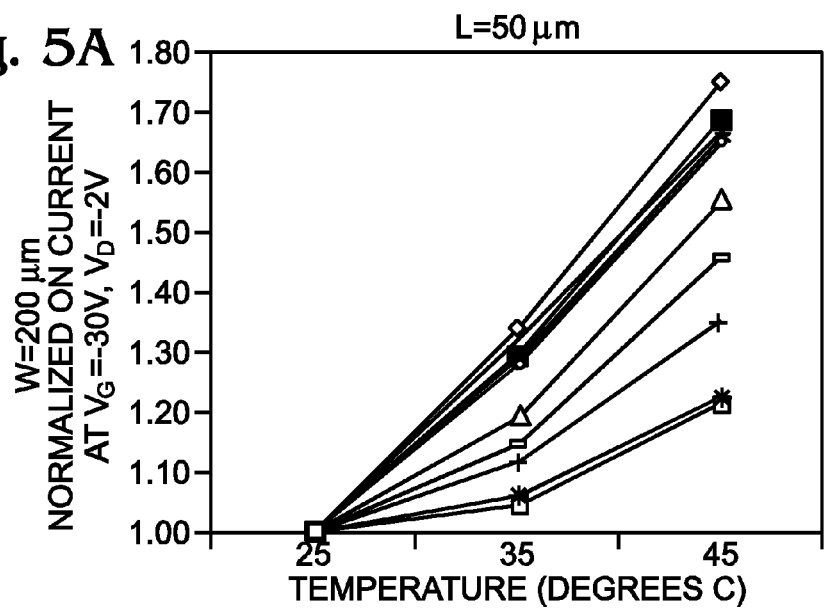

Thus, when environmental condition 1 changes for example, the TFT resistance R (and ONLY the TFT resistance) changes. When environmental condition 2 changes, the capacitance C (and ONLY the capacitance) changes. The relationship between current amplitude |Iac|, phase (<Iac), R, and C is shown in FIG. 3 (when the series-connected TFT is approximated by its channel resistance R). These relationships are well understood in the art.

In one simple example, some or all of the sensel TFTs have a $R_{DS}$ responsive to temperature as the first environmental condition. Alternatively, some or all the sensel TFTs 108 may comprise a gate dielectric sensitive to a moisture first environmental condition, with the $R_{DS}$ responsive to changes in the moisture content of the gate dielectric. As another alternative, some or all of the sensel TFTs 108 may comprise a gate dielectric sensitive to a force or pressure first environmental condition, with the $R_{DS}$ responsive to changes in the force or pressure applied upon the gate dielectric region of the TFT.

If the passive element 110 is a capacitor, it may be comprised of a dielectric sensitive to a second environmental condition such as pressure, moisture, chemicals, solution pH, oxygen, salinity, and shear, with a capacitance responsive to the second environmental condition. For example, a tin dioxide dielectric can be used to measure oxygen content, and a metal-insulator-semiconductor capacitor can be used to measure pH.

Figure 2:
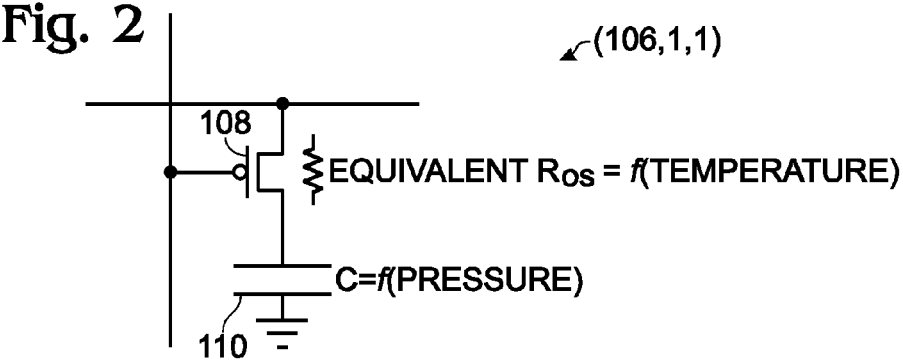
FIG. 2 is a schematic diagram of an exemplary sensel.

FIG. 2 is a schematic diagram of an exemplary sensel (106, 1, 1). The sensel comprises a switching device 108 (e.g., a PMOS TFT), which is also sensitive to temperature. Thus, the effective mobility and/or the threshold voltage of the transistor varies monotonically with temperature. It can therefore be postulated that the equivalent drain-to-source resistance of the device $R_{DS}$ is a function of temperature. In this example, the passive sensing element 110 is a capacitor. The capacitance of the sensor varies with the force applied to the sensel.

FIG. 3 is an equivalent circuit of the sensel depicted in FIG. 2. The operating principle of this exemplary sensel is based on determining the R and C components of an RC circuit stimulated by a single AC current or voltage measurement. A particular sensel in the array is activated by applying a DC signal at the gate line (turning the TFT ON) and an AC voltage at the data line, and measuring $I_{ac}$. Here it is assumed that the R component is the source-drain resistance of a TFT $R_{DS}$, which is a function of temperature T (and not affected by pressure). It is further assumed that C is a passive capacitive sensor, whose capacitance is a function of the applied pressure (and not affected by temperature). The dependence of the AC current (amplitude and phase) flowing through the sensel when the TFT is in the ON state to R and C is shown. Therefore, two physical quantities (temperature and pressure in this aspect) can be determined by a single AC current measurement of the sensel. If the passive device is an inductor, then R and L components are measured. In one variation not shown, AC measurements may be taken at a terminal located between the TFT and the passive device.

Typically, in a conventional active-matrix circuit, the TFT is utilized only as an ON/OFF switch. In the sensor array described herein, the TFT is engineered in a way that, when the TFT is ON, the drain-to-source current is also a function of a physical quantity X (e.g., temperature). At the same time, the passive element's electrical characteristics (capacitance or inductance) is a function of another physical quantity Y (e.g., force, moisture, etc.). Ideally the sensitivity of the sensor element designed for sensing X (or Y) to Y (or X) is zero.

Using a single AC impedance, the phase and amplitude of current through the sensel is measured. The amplitude and phase are determined by the R-C or R-L components of the sensel (R is dominated by the TFT, and C/L by the capacitance/inductance of the passive element). Since R=f(X) and C=f(Y), amplitude and phase can be used to calculate X and Y.

Figure 4:
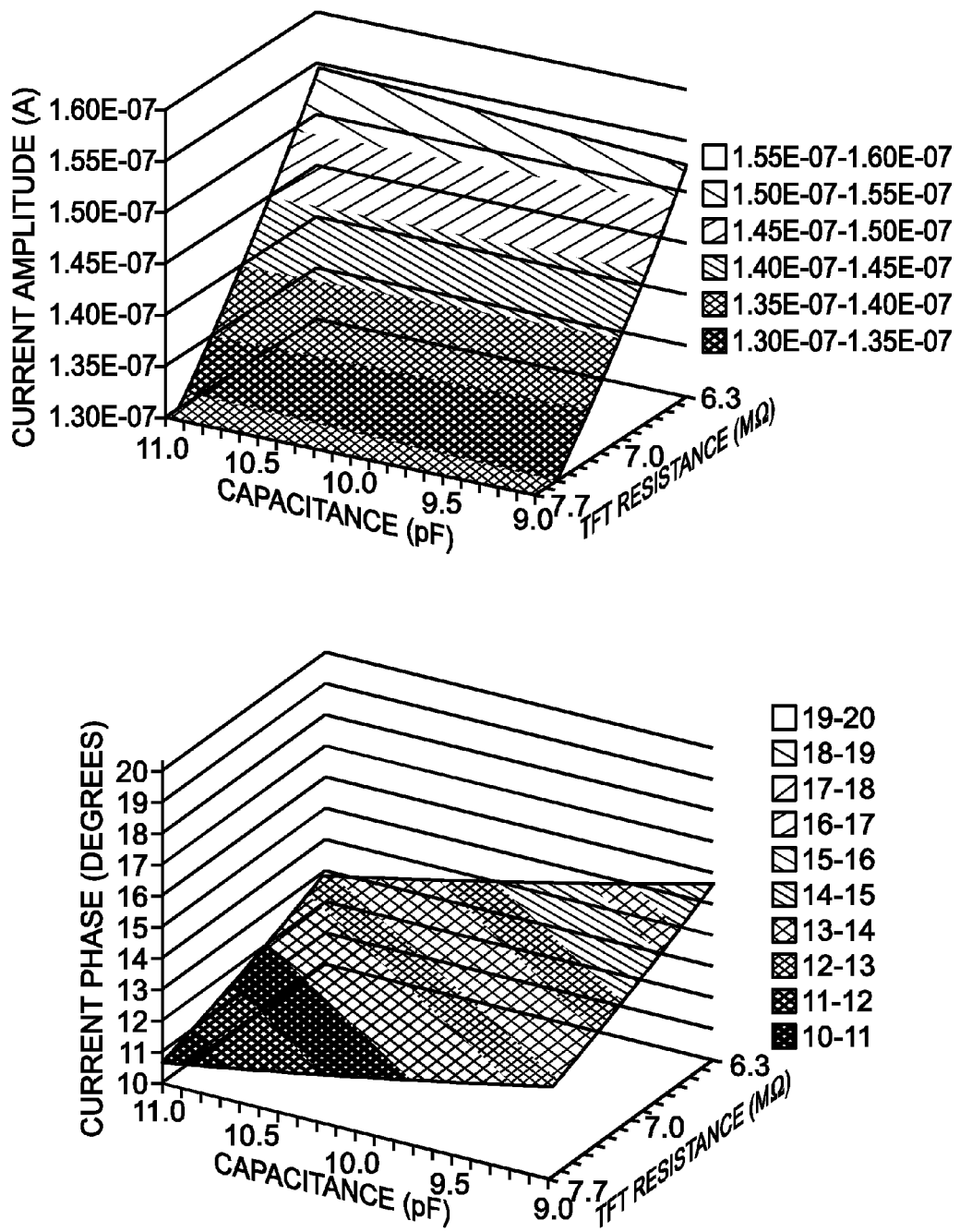
FIG. 4 depicts graphed simulation results of the amplitude and phase of the AC current through a sensel comprising of a TFT and a capacitor.
Figure 5F:
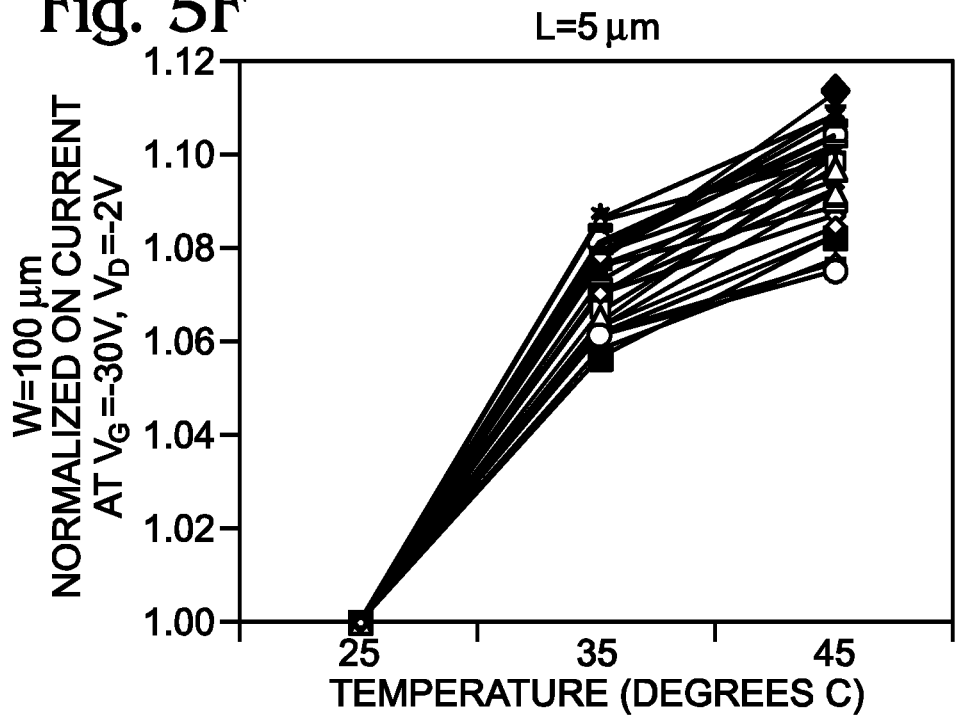

FIG. 4 depicts graphed simulation results of the amplitude and phase of the AC current through a sensel comprising of a TFT and a capacitor. The sensel is driven by an AC voltage source, 1 V, 10 kHz. The TFT is supposed to have an ON resistance of 7 MΩ, which varies by ±10%. The capacitor is supposed to have a capacitance of 10 pF, which varies by ±10%. This variation is supposed to be due to two different physical quantities (e.g., resistance varying due to temperature, and capacitance varying due to force).

As seen in the figure, the TFT resistance (the R component) variation is mainly reflected in the measured amplitude of the AC signal. On the other hand, variation of capacitance (the C component), as well as R, results in AC signal phase variation.

As depicted in FIG. 1, driving and read-out of the array is accomplished simultaneously. Gate driver and data driver circuits, which may be located externally, or mounted on the substrate (as shown) are used to connect the AC impedance meter circuitry to one array sensel at a time. The Gate and Data drivers comprise a series of ON/OFF switches, and be realized by semiconductor switches (transistor-based), electromagnetic relays, or other devices of similar function. Likewise, the AC impedance meter applies an AC voltage signal of one or multiple frequencies between its two terminals, and measures the resulting AC current (or voltage).

In one exemplary sensor array the active-matrix is realized with sensels comprising p-type thin-film transistors and capacitive pressure sensors. The TFT uses an organic, pentacene-based semiconductor, whose ON resistance is a function of temperature. The variation of ON resistance to pressure is negligible.

FIGS. 5A through 5F are graphs showing the variation of the normalized ON current of TFTs of various channel dimensions (width W and length L) as a function of temperature. Note that the TFT drain-source resistance is inversely proportional to its ON current.

Figure 6:
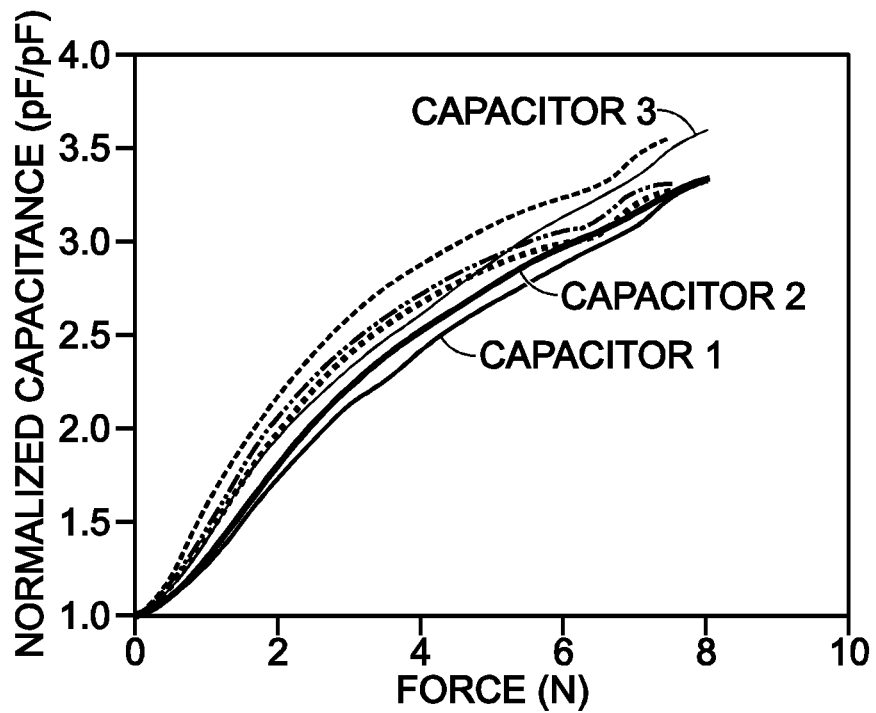
FIG. 6 is a graph depicting the variation of normalized capacitance of a pressure-sensitive sensel capacitor as a function of force applied normal to the capacitor surface.

FIG. 6 is a graph depicting the variation of normalized capacitance of a pressure-sensitive sensel capacitor as a function of force applied normal to the capacitor surface. The pressure-sensitive capacitor in this example is implemented as a parallel-plate element, with a low-modulus compressible polymer dielectric. The figure shows the variation of the normalized capacitance of the capacitive force sensor as a function of force applied on a 1 cm$^2$ area. The response of multiple elements is shown.

Figure 7A:
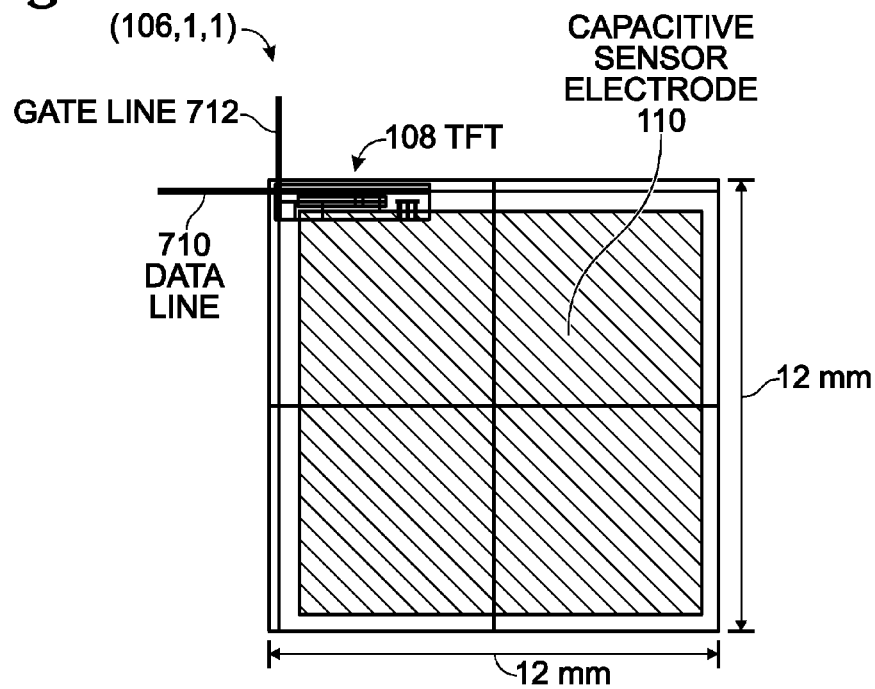
FIGS. 7A and 7B are, respectively, plan and partial cross-sectional views of an exemplary practical realization of a sensel.
Figure 7B:
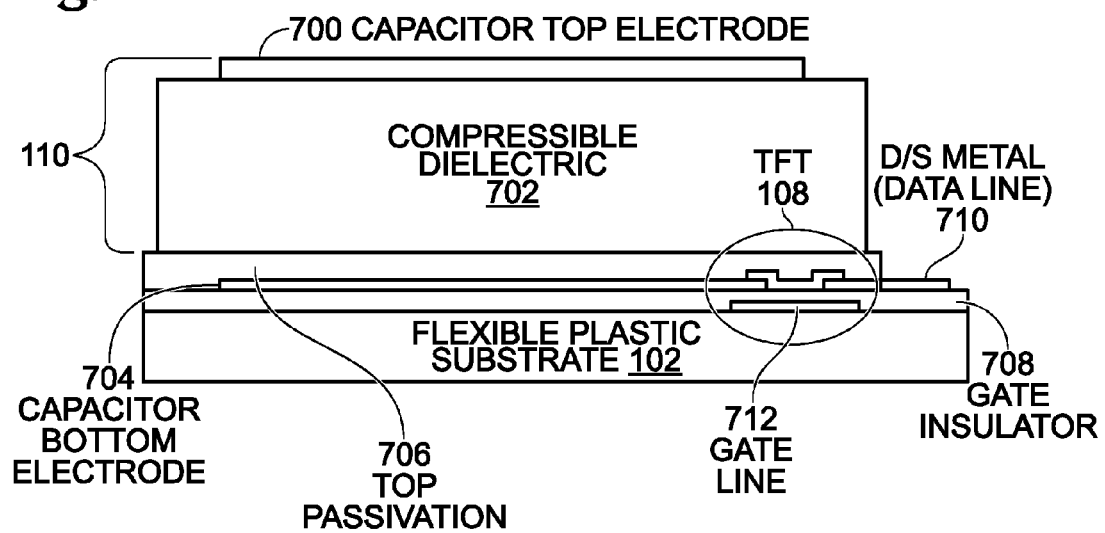

FIGS. 7A and 7B are, respectively, plan and partial cross-sectional views of an exemplary practical realization of a sensel. Here the capacitor 110 includes a top electrode 700, compressible dielectric 702, and bottom electrode 704. A top passivation layer 706 is interposed between the dielectric 702 and bottom electrode 704. A gate insulator 708 is shown underlying the drain/source (D/S) line 710, and overlying gate line 712.

Figure 8A:
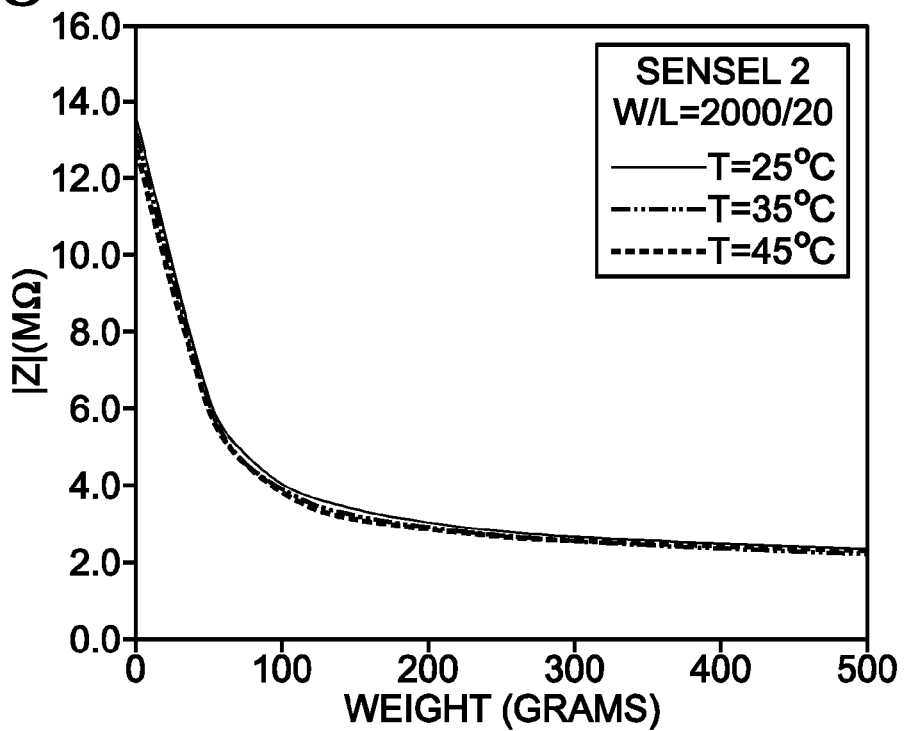
FIGS. 8A and 8B are graphs depicting experimental response data for an exemplary sensel.
Figure 8B:
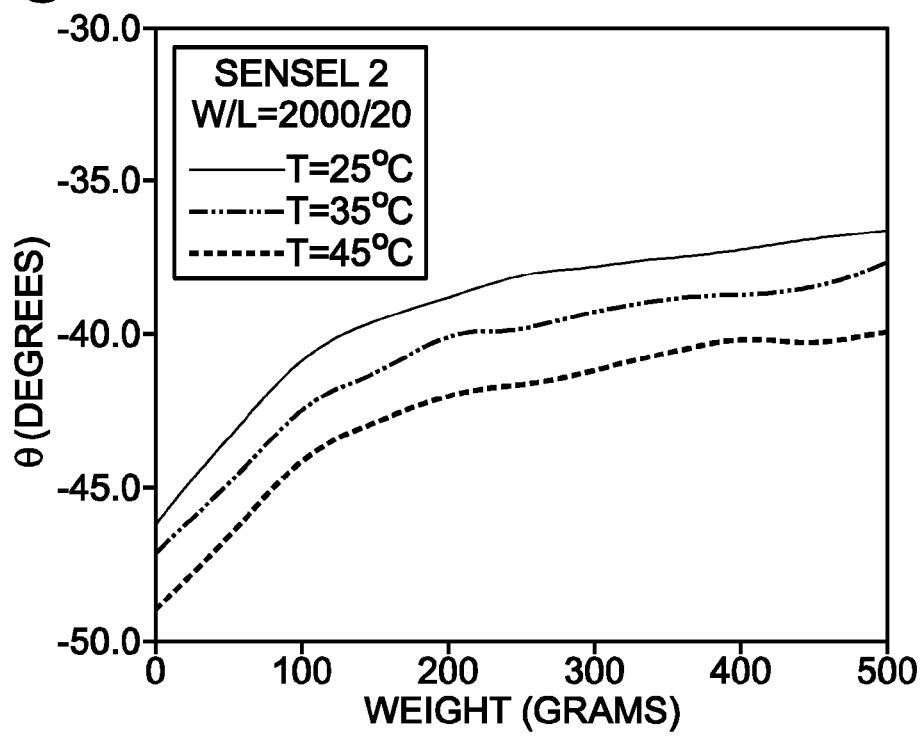

FIGS. 8A and 8B are graphs depicting experimental response data for an exemplary sensel. In this figure, the experimental amplitude and phase of the sensel impedance is shown, with a 1 V (rms) voltage excitation at 10 kHz. The amplitude and phase is plotted as a function of the applied weight (in grams) over the sensel area (1 cm$^2$) at three different temperatures. Note that the single AC measurement makes it possible to distinguish both temperature and force (pressure), in a trend that is consistent with the simulated results of FIG. 4.

It should be understood that the sensor array can be configured with multiple types of sensels, where each type of sensel includes a different type of passive device, to measure different environmental conditions. Alternatively, the sensels may all include the same type of passive elements (e.g., a capacitor), but of different types (e.g., with different types of dielectric) to measure different environmental conditions. Likewise, multiple types of TFTs may be used to measure different environmental conditions. In this manner, a single sensor array can measure multiple (more than two) environmental conditions.

FIG. 9 is a flowchart illustrating a method for making multiple environmental measurements using a single sensing element. Although the method is depicted as a sequence of numbered steps for clarity, the numbering does not necessarily dictate the order of the steps. It should be understood that some of these steps may be skipped, performed in parallel, or performed without the requirement of maintaining a strict order of sequence. Generally however, the method follows the numeric order of the depicted steps. The method starts at Step 900.

Step 902 provides a sensel including a TFT and a passive element. Step 904 accepts a first electrical stimulus. In response to the first electrical stimulus, Step 906 supplies a first electrical measurement responsive to a change in TFT electrical characteristic correlated to a first environmental condition, as well as a change in a characteristic of the passive element correlated to a second environmental condition. The first and second environmental conditions include temperature, pressure, moisture, chemicals, oxygen, solution pH, salinity, and shear. In response to supplying the first electrical measurement, Step 908 determines the first environmental condition independent of the second environmental condition, and Step 910 determines the second environmental condition independent of the first environmental condition.

In one aspect, accepting the first electrical stimulus in Step 904 includes substeps. Step 904a accepts a DC voltage at a gate electrode of the sensel TFT. Step 904b simultaneously accepts an AC signal at the drain electrode or source electrode of the sensel TFT. The AC signal accepted in Step 904b has a first amplitude and a first phase. Then, Step 906 supplies the AC signal with a second amplitude, different than the first amplitude, and a second phase, different than the first phase. In one variation, Step 904b accepts a plurality of AC signals at different frequencies, where each AC signal frequency has a predetermined amplitude and predetermined phase. In this variation Step 906 supplies a change and amplitude and phase for each of the accepted frequencies.

In one example, Step 906 supplies the first electrical measurement in response to the TFT characteristics being channel resistance or source-to-drain resistance ($R_{DS}$). The TFT $R_{DS}$ may, for example, be responsive to temperature as the first environmental condition. In another variation, the TFT may have a gate dielectric sensitive to a moisture first environmental condition, with the $R_{DS}$ responsive to changes in the moisture content of the gate dielectric. In another example, the TFT comprises with a gate dielectric sensitive to a force or pressure first environmental condition, with the $R_{DS}$ responsive to changes in the force or pressure applied upon the gate dielectric region of the TFT.

In another example, Step 902 provides a sensel with a capacitor having a dielectric sensitive to a second environmental condition such as pressure, moisture, chemicals, solution pH, oxygen, salinity, and shear, with a capacitance responsive to the second environmental condition.

Typically, Step 902 provides a plurality of sensels arranged in an addressable array (see FIG. 1). Step 903 arranges the array of sensels over a surface. Then, Step 906 supplies a plurality of electrical measurements responsive to first and second environmental conditions at a corresponding plurality of locations on the surface.

A dual-function sensor array and associated monitoring method have been provided. Examples of particular hardware elements and exemplary environmental conditions have been presented to illustrate the invention. However, the invention is not limited to merely these examples. Although the invention has been presented as a device for monitoring only two conditions in the interest of simplicity, it should be understood that a sensel may include multiple TFTs and/or multiple passive elements to monitor more than two conditions. Likewise, different types of two-element (or multi-element) sensels may be arranged in an array for a similar purpose. Other variations and embodiments of the invention will occur to those skilled in the art.

I claim:

1. A dual-function active matrix sensor array comprising:
a substrate with a top surface;
a plurality of sensing elements (sensels) formed in an array overlying the substrate top surface, each sensel comprising:
a thin-film transistor (TFT) having a channel resistance or source-to-drain resistance ($R_{DS}$) responsive to a first environmental condition;
a passive element having an AC impedance responsive to a second environmental condition, different than the first environment condition; and,
a measurement device selectively connectable to each sensel in the array to simultaneously determine first environmental condition measurements and second environmental condition measurements, wherein:
the measurement device supplies an AC signal having a predetermined first amplitude and predetermined first phase, and makes a first environmental condition determination and a second environmental condition determination in response to detecting a change in the AC signal amplitude with respect to the AC signal first amplitude, and a change in AC signal phase with respect to the AC signal first phase.

2. The sensor array of claim 1 further comprising:
a DC voltage source;
a gate driver switching network to selectively connect a gate electrode of each sensel TFT to the DC voltage source.

3. The sensor array of claim 2 further comprising:
a data driver switching array to selectively connect a drain electrode or source electrode of each sensel TFT to the measurement device, simultaneous with the gate driver switching network connecting the gate of the corresponding TFT to the DC voltage source.

4. The sensor array of claim 1 wherein the passive element is selected from the group consisting of a capacitor, parallel-plate, co-planar interdigitated electrode, metal-oxide-semiconductor (MOS) capacitor, and an inductor.

5. The sensor array of claim 1 wherein the first and second environmental conditions are selected from a group consisting of temperature, pressure, moisture, chemicals, oxygen, solution pH, salinity, and shear.

6. The sensor array of claim 1 wherein the measurement device has a user output to supply a map of first and second environmental conditions, cross-referenced to sensel locations in the array.

7. The sensor array of claim 1 wherein the measurement device detects a first AC signal amplitude change and a first AC signal phase change and determines the first environmental conditions independent of second environmental condition measurements, and determines the second environmental conditions independent of first environmental condition measurements.

8. The sensor array of claim 1 wherein each sensel TFT $R_{DS}$ is responsive to temperature as the first environmental condition.

9. The sensor array of claim 1 wherein each sensel TFT comprising a gate dielectric sensitive to a moisture first environmental condition, with the $R_{DS}$ responsive to changes in the moisture content of the gate dielectric.

10. The sensor array of claim 1 wherein the passive element is a capacitor comprising a dielectric sensitive to a second environmental condition selected from the group consisting of pressure, moisture, chemicals, solution pH, oxygen, salinity, and shear, with a capacitance responsive to the second environmental condition.

11. The sensor array of claim 1 wherein each sensel TFT comprising a gate dielectric sensitive to a force or pressure first environmental condition, with the $R_{DS}$ responsive to changes in the force or pressure applied upon the gate dielectric region of the TFT.

12. The sensor array of claim 1 wherein the measurement device supplies an AC signal at a plurality of frequencies, each AC signal frequency having a predetermined amplitude and phase, and makes a first environmental condition determination and a second environmental condition determination in response to detecting a change in the plurality of AC signals.

13. A method for making multiple environmental measurements using a single sensing element, the method comprising:
providing a sensing element (sensel) including a thin-film transistor (TFT) and a passive element, the sensel TFT having a gate electrode, a drain electrode, and a source electrode;
accepting a first electrical stimulus, wherein accepting the first electrical stimulus includes:
accepting a DC voltage at the gate electrode of the sensel TFT; and,
simultaneously accepting an AC signal at the drain electrode or source electrode of the sensel TFT;
in response to the first electrical stimulus, supplying a first electrical measurement responsive to:
a change in TFT electrical characteristic correlated to a first environmental condition; and,
a change in a characteristic of the passive element correlated to a second environmental condition.

14. The method of claim 13 wherein accepting the AC signal include accepting an AC signal with a first amplitude and a first phase; and,
wherein supplying the first electrical measurement includes supplying the AC signal with a second amplitude, different than the first amplitude, and a second phase, different than the first phase.

15. The method of claim 14 wherein accepting the AC signal includes accepting a plurality of AC signals at different frequencies, each AC signal frequency having a predetermined amplitude and predetermined phase.

16. The method of claim 13 wherein supplying the first electrical measurement includes supplying the first electrical measurement in response first and second environmental conditions selected from a group consisting of temperature, pressure, moisture, chemicals, oxygen, solution pH, salinity, and shear.

17. The method of claim 13 further comprising:
in response to supplying the first electrical measurement, determining the first environmental condition independent of the second environmental condition; and,
in response to supplying the first electrical measurement, determining the second environmental condition independent of the first environmental condition.

18. The method of claim 13 wherein supplying the first electrical measurement in response to the TFT characteristics includes the TFT characteristics being channel resistance or source-to-drain resistance ($R_{DS}$).

19. The method of claim 18 wherein the TFT $R_{DS}$ is responsive to temperature as the first environmental condition.

20. The method of claim 18 wherein providing the sensel includes providing a TFT with a gate dielectric sensitive to a moisture first environmental condition, with the $R_{DS}$ responsive to changes in the moisture content of the gate dielectric.

21. The method of claim 13 wherein providing the sensel passive element includes providing a sensel with a capacitor having a dielectric sensitive to a second environmental condition selected from the group consisting of pressure, moisture, chemicals, solution pH, oxygen, salinity, and shear, with a capacitance responsive to the second environmental condition.

22. The method of claim 13 wherein providing the sensel includes providing a TFT comprising a gate dielectric sensitive to a force or pressure first environmental condition, with the $R_{DS}$ responsive to changes in the force or pressure applied upon the gate dielectric region of the TFT.

23. The method of claim 13 wherein providing the sensel including the TFT and a passive element includes providing a plurality of sensels arranged in an addressable array;
   the method further comprising:
   arranging the array of sensels over a surface; and,
   wherein supplying a first electrical measurement includes supplying a plurality of electrical measurements responsive to first and second environmental conditions at a corresponding plurality of locations on the surface.

\* \* \* \* \*